United States Patent [19]

Aoki et al.

[11] 4,341,774
[45] Jul. 27, 1982

[54] METHOD FOR SUPPRESSING ABNORMAL RISE IN IMMUNOLOGICAL FUNCTION AND AGENT USEFUL THEREFOR

[75] Inventors: Takao Aoki; Hideo Miyakoshi; Yoshihei Hirasawa, all of Niigata; Yasuo Nishii, Tokyo, all of Japan

[73] Assignee: Chugai Seiyaku Kabushiki Kaisha, Tokyo, Japan

[21] Appl. No.: 176,642

[22] Filed: Aug. 11, 1980

[30] Foreign Application Priority Data

Aug. 10, 1979 [JP] Japan ................................. 54-101211

[51] Int. Cl.³ .......................................... A01N 45/00
[52] U.S. Cl. ............................................. 424/236
[58] Field of Search ...................... 424/236; 260/397.2

[56] References Cited

U.S. PATENT DOCUMENTS

| | | | |
|---|---|---|---|
| 3,639,596 | 2/1972 | DeLuca et al. | 260/397.2 |
| 3,715,374 | 2/1972 | DeLuca | 260/397.2 |
| 3,739,001 | 6/1973 | DeLuca | 260/397.2 |
| 3,741,996 | 6/1973 | DeLuca et al. | 260/397.2 |
| 3,847,955 | 11/1974 | DeLuca | 260/397.2 |
| 4,022,768 | 5/1977 | Matsunaga et al. | 260/397.2 |
| 4,022,891 | 5/1977 | Takeshita et al. | 260/239.55 |
| 4,164,569 | 8/1979 | Ikushima et al. | 424/236 |
| 4,195,027 | 3/1980 | DeLuca et al. | 260/397.2 |

FOREIGN PATENT DOCUMENTS

| | | | |
|---|---|---|---|
| 1069939 | 2/1976 | Canada | 260/397.2 |
| 1077028 | 6/1979 | Canada | 260/397.2 |
| 51-26858 | of 1976 | Japan | 260/397.2 |
| 51-26859 | of 1976 | Japan | 260/397.2 |
| 52-71456 | of 1977 | Japan | 260/397.45 |

*Primary Examiner*—Elbert L. Roberts
*Attorney, Agent, or Firm*—Browdy and Neimark

[57] ABSTRACT

A method for suppressing abnormal rise in immunological function which often causes various types of autoimmune diseases, and an agent useful therefor are disclosed. The method is carried out by administering cholecalciferol or its derivative to patients suffering from abnormal rise in immunological function. The agent contains the above compound as active ingredient and is useful not only to treat and/or prevent the abnormal rise in immunological function but also to suppress graft rejection.

7 Claims, No Drawings

METHOD FOR SUPPRESSING ABNORMAL RISE IN IMMUNOLOGICAL FUNCTION AND AGENT USEFUL THEREFOR

This invention relates to a method for suppressing abnormal rise in immunological function and an agent useful therefor.

Many diseases are known to be caused by abnormal rise in immunological function. The diseases include so called autoimmune diseases such as chronic thyroiditis, autoimmune hemolytic, rheumatoid arthritis, systemic lupus erythematosus and the like. The method and agent of this invention are useful not only for treatment or prevention of such diseases, but also for suppression of graft rejection.

For the same purpose, some compounds such as steroid hormone, azathiopurine, and cyclophosphamide have been used, but they are not completely satisfactory because of their low activity or undesired side-effects.

During study by the inventors to develop a new drug for the above use, they found surprisingly that cholecalciferol (referred to as $D_3$ hereunder) or its derivative which is used as an anti-rickets agent was useful not only to control calcium metabolism but also to suppress the immunological function.

The inventors continued their studies based on this fact and finally completed this invention, which relates to a method for suppressing abnormal rise in immunological function by administration of $D_3$ or its derivative, and an agent containing the same.

Since there is no report showing or suggesting that $D_3$ or its derivative has immunological function, this invention is believed to be based on a new discovery by the inventors.

$D_3$ which is useful in this invention is present in tuna liver oil, and it is also known that it can be synthesized from 7-dehydrocholesterine by irradiating it with UV radiation. Thus, it is a well-known compound, but has been used heretofore only as an anti-rickets drug.

In addition to $D_3$ above, many derivatives thereof can be used as an active component in the method or the agent of this invention. The derivatives include, for example, hydroxyl-containing $D_3$ such as 1α-hydroxycholecalciferol (1α—OH—$D_3$); 25-hydroxycholecalciferol (25—OH—$D_3$); 24(R)-hydroxycholecalciferol (24(R)—OH—$D_3$); 24(S)-hydroxycholecalciferol (24(S)—OH—$D_3$); 1α,25-dihydroxycholecalciferol (1α,25—(OH)$_2$—$D_3$); 1α,24(R)-dihydroxycholecalciferol (1α,24(R)—(OH)$_2$—$D_3$); 1α,24(S)-dihydroxycholecalciferol (1α,24—(OH)$_2$—$D_3$); 24,25-dihydroxycholecalciferol (24,25—(OH)$_2$—$D_3$); 25,26-dihydroxycholecalciferol (25,26—(OH)$_2$—$D_3$); 1α,24,25-trihydroxycholecalciferol (1α,24,25—(OH)$_3$—$D_3$); or the like.

All of the above exemplified derivatives are known compounds and can be prepared by the methods disclosed in, for example, Japanese Patent Disclosures Nos. 62750/73, 26858/76, 26859/76, 100056/76 and 71456/77; U.S. Pat. Nos. 3,639,596; 3,715,374; 3,847,955; and 3,739,001;

According to this invention, the active compound is formulated into a desired form in a conventional manner and administered to patients. The form of agent is not critical in this invention. However, since the dose of the active compound is very small, for example, in an amount such that the concentration in blood is from 0.01 to 1 μg/ml, it is preferred to formulate the compound into soft capsules for oral administration.

Although the amount of the active ingredient incorporated in a minimum dosage form such as a single capsule, tablet, pill or packet of powder or packet of granule is not critical, it is preferably from 0.1 to 5 μg.

According to this invention, $D_3$ or its derivative is usually administered in an amount of from 0.25 to 10 μg/day, preferably from 0.5 to 5 μg/day per adult.

This invention is further illustrated by the following Experiment and Examples. However, they should not be construed to limit this invention in any sense.

EXPERIMENT

Venous blood from healthy adults was anticoagulated with heparin, and blended with the equivalent volume of physiological saline, and the mixture was added to Ficoll-Conray solution. After centrifugation at 400×G for 30 minutes, lymphocytes were isolated from the mixture and washed three times with Hank's balanced salt solution.

The lymphocytes were suspended in a concentration of $1.5 \times 10^6$ cells/ml in RPMI 1640 culture medium which had been supplemented with penicillin G (100 IU/ml), streptomycin (100 μg/ml) and 20% of heat inactivated calf serum.

The cell suspension (100 μl) was placed in a hole of micro test II plate, and a cell division accelerating substance (referred to as mitogen hereunder) and test plasma as well as RPMI 1640 culture medium were added to the suspension to make the total volume of the mixture 200 μl. The culture plate was incubated in a humidified atmosphere of 95% air and 5% $CO_2$ at 37° C. Twenty-four hours before the completion of the incubation, 0.1 μCi of methyl-$H^3$-thymidine (specific activity 5 Ci/mmol) was added to the mixture.

After completion of the incubation, the lymphocites were recovered by filtration with glass fibers, and the amount of isotope incorporated in the cells was counted with a liquid scintillation counter. In the experiments above, phytohemagglutinin (PHA) or Concanavalin A (Con A) was used as T-cell mitogen and staphage lysate (SPL) was used as T- and B-cell mitogen. In case PHA was used, the incubation was effected for 72 hours, on the other hand, 120 hour incubation was made for Con A or SPL.

Incidentally, in order to observe the normal increase in DNA synthesis, a blank test omitting addition of the mitogen was run in parallel at 120 hour incubation to determine the amount of the bound methyl-$H^3$-thymidine.

The results of the test are shown in the following Table. The figures in the table represent counts per minute (cpm) as the mean and standard error.

| Test Compound | Concentration in Blood (μg/ml) | PHA | SPL | Con A | without Mitogen |
|---|---|---|---|---|---|
| 1α—OH—$D_3$ | 0.1 | — | 16311 ± 1281 | 13117 ± 191 | 93 ± 14 |
| 25-OH—$D_3$ | 0.1 | 2160 ± 352 | 21062 ± 460 | 14897 ± 689 | 152 ± 51 |

-continued

| Test Compound | Concentration in Blood (μg/ml) | PHA | SPL | Con A | without Mitogen |
|---|---|---|---|---|---|
| 24(R)—OH—$D_3$ | 0.1 | 21082 ± 922 | 17408 ± 454 | 11355 ± 130 | 185 ± 71 |
| 24(S)—OH—$D_3$ | 0.01 | 19884 ± 1436 | — | — | 138 ± 22 |
|  | 0.1 | 19925 ± 1728 | 20188 ± 906 | 16491 ± 846 | 153 ± 15 |
| 1α,25-$(OH)_2$—$D_3$ | 0.0001 | — | 16855 ± 643 | 13180 ± 733 | 131 ± 16 |
|  | 0.001 | 19311 ± 243 | 14006 ± 300 | 10680 ± 251 | 135 ± 20 |
|  | 0.01 | 18933 ± 215 | 12102 ± 228 | 10457 ± 832 | 156 ± 3 |
|  | 0.1 | 19699 ± 320 | 11605 ± 712 | 9846 ± 595 | 133 ± 36 |
| 1α,24(R)—$(OH)_2$—$D_3$ | 0.0001 | 16023 ± 1016 | 18530 ± 879 | 12979 ± 630 | 100 ± 15 |
|  | 0.001 | 15267 ± 817 | 14788 ± 172 | 10215 ± 943 | 143 ± 10 |
|  | 0.01 | 14667 ± 527 | 12999 ± 164 | 9687 ± 599 | 138 ± 13 |
|  | 0.1 | 17075 ± 718 | 12743 ± 763 | 8750 ± 660 | 127 ± 5 |
| 1α,24(S)—$(OH)_2$—$D_3$ | 0.001 | 21362 ± 1429 | 16902 ± 701 | 13818 ± 1094 | 107 ± 7 |
|  | 0.01 | 18279 ± 544 | 12869 ± 482 | 10788 ± 349 | 150 ± 17 |
|  | 0.1 | 20085 ± 755 | 12642 ± 687 | 8850 ± 450 | 133 ± 35 |
| Control | — | 23498 ± 976 | 22652 ± 1334 | 17397 ± 208 | 138 ± 22 |

EXAMPLE 1

One mg of 24(R)—OH—$D_3$ was dissolved in 60 g of corn oil and to the solution was added 6 mg of dibutylhydroxytoluene as a stabilizer. By the conventional way using a capsule filler, the mixture was formulated into soft gelatin capsules containing 1 μg of 24(R)—OH—$D_3$ per capsule.

EXAMPLE 2

1α,25—$(OH)_2$—$D_3$ (0.25 mg) was dissolved in 60 g of O.D.O. (triglyceride of medium chain fatty acid: manufactured by Nisshin Seiyu Kabushiki Kaisha, Japan). To the solution was added 30 mg of sorbic acid as a stabilizer. By the conventional way using a capsule filler, the solution was formed into soft capsules each containing 0.25 μg of 1α,25—$(OH)_2$—$D_3$.

EXAMPLE 3

Example 2 was repeated except that 0.5 mg of 1α,24(R)—$(OH)_2$—$D_3$ was used instead of 0.25 mg of 1α,25—$(OH)_2$—$D_3$ to form soft capsules containing 0.5 μg of 1α,24(R)—$(OH)_2$—$D_3$ per capsule.

EXAMPLE 4

1α,24(S)—$(OH)_2$—$D_3$ was dissolved in corn oil containing 0.5% of potassium sorbate to make the concentration of the $D_3$ derivative 10 μg/ml. By the conventional way using a capsule filler, soft gelatin capsules containing 1 μg of 1α,24(S)—$(OH)_2$—$D_3$ each were formed.

EXAMPLE 5

24(S)—OH—$D_3$ was dissolved in olive oil containing 0.01% of propyl gallate to form a solution containing 10 μg/ml of the $D_3$ derivative. By the conventional way using a capsule filler, soft gelatin capsules containing 1 μg of 24(S)—OH—$D_3$ each were prepared.

We claim:

1. A method for immunosuppression in humans which comprises administering cholecalciferol and/or its derivative to a human in need of immunosuppression, in an amount sufficient to suppress abnormal rise in immunological function.

2. A method according to claim 1 wherein said cholecalciferol and/or its derivative is administered in an amount of from 0.25 to 10 μg/day per adult.

3. A method according to claim 2 wherein said amount is from 0.5 to 5 μg/day per adult.

4. A method according to claim 1 wherein said cholecalciferol and/or its derivative is administered in an amount such that the concentration in blood of the active ingredient is from 0.01 μg/ml to 1 μg/ml.

5. A method in accordance with claim 1 wherein said cholecalciferol and/or its derivative is administered to a human having an autoimmune disease.

6. A method in accordance with claim 5 wherein said autoimmune disease is chronic thyroiditis, autoimmune hemolytic rheumatoid arthritis, or systemic lupus erythematosus.

7. A method in accordance with claim 1 wherein said cholecalciferol and/or its derivative is administered to a human in need of suppression of graft rejection.

* * * * *